United States Patent
Resendiz-Hernandez

(10) Patent No.: US 10,188,610 B2
(45) Date of Patent: Jan. 29, 2019

(54) PROLONGED-RELEASE DIPHENIDOL COMPOSITION

(71) Applicant: INVEKRA, S.A.P.I. DE C.V., México, D.F (MX)

(72) Inventor: Guadalupe Resendiz-Hernandez, Estado de Mexico (MX)

(73) Assignee: INVEKRA, S.A.P.I. DE C.V., Mexico, D.F. (MX)

( * ) Notice: Subject to any disclaimer, the term of this patent is extended or adjusted under 35 U.S.C. 154(b) by 0 days.

(21) Appl. No.: 14/759,683

(22) PCT Filed: Jan. 15, 2014

(86) PCT No.: PCT/IB2014/000044
§ 371 (c)(1),
(2) Date: Jul. 8, 2015

(87) PCT Pub. No.: WO2014/111799
PCT Pub. Date: Jul. 24, 2014

(65) Prior Publication Data
US 2015/0352051 A1    Dec. 10, 2015

(30) Foreign Application Priority Data
Jan. 16, 2013 (MX) .................... MX/a/2013/000662

(51) Int. Cl.
*A61K 9/20* (2006.01)
*A61K 31/4453* (2006.01)

(52) U.S. Cl.
CPC ............ *A61K 9/2054* (2013.01); *A61K 9/205* (2013.01); *A61K 9/2009* (2013.01); *A61K 9/2013* (2013.01); *A61K 9/2027* (2013.01); *A61K 9/2077* (2013.01); *A61K 31/4453* (2013.01)

(58) Field of Classification Search
None
See application file for complete search history.

(56) References Cited

U.S. PATENT DOCUMENTS 4,702,918 A * 10/1987 Ushimaru ............ A61K 9/0065
424/461
8,574,625 B2 * 11/2013 Jain ...................... A61K 9/2072
424/465

FOREIGN PATENT DOCUMENTS

CN        1935140        3/2007

OTHER PUBLICATIONS

Aljaberi et al. (Functional performance of silicified microcellulose versus microcrystalline cellulose: a case study; Drug Development and Industrial Pharmacy, 2009;35(9): 1066-1071.*

(Continued)

*Primary Examiner* — Robert A Wax
*Assistant Examiner* — Melissa S Mercier
(74) *Attorney, Agent, or Firm* — Browdy and Neimark, P.L.L.C.

(57) ABSTRACT

A sustained release diphenidol pharmaceutical composition is described, comprising: a) from 15 to 50% diphenidol hydrochloride; b) from 0.1 to 20% of one or more binding agents; c) from 5 to 90% of one or more diluent agents; d) from 5 to 50% of one or more releasing modification agents; e) from 0.25 to 10% of one or more lubricating agents; and f) 0.1 to 10% of one or more gliding agents.
Preferably, this pharmaceutical composition is orally administered and is in tablet form.

15 Claims, 3 Drawing Sheets

(56) References Cited

OTHER PUBLICATIONS

Aljaberi et al. (Functional performance of silicified microcellulose versus microcrystalline cellulose: a case study; Drug Development and Industrial Pharmacy, 2009;35(9): 1066-1071. (Year: 2009).*

* cited by examiner

PROLONGED-RELEASE DIPHENIDOL COMPOSITION

FIELD OF THE INVENTION

The present invention is related to the pharmaceutical industry, and more particularly it is related to a sustained release diphenidol composition.

BACKGROUND OF THE INVENTION

Diphenidol (α,α-diphenil-1-piperidinebutanol) is a drug which has been used for a long time as an antiemetic and anti vertigo agent. The base of the antiemetic effect is found in the brain, specifically in the action sites at the chemoreceptor trigger zone in the area postrema. Likewise, its anti vertigo effect is attributed to its action in the vestibular apparatus (Leung et al., Pharmacological Reports. 2012, 64, 739-744). Diphenidol hydrochloride is the most used salt of this active principle.

Diphenidol is indicated to prevent and control nausea and vomiting caused by diseases affecting kidneys, liver, gall bladder and gastrointestinal tract, as well as those caused by labyrinth alterations, malignant neoplasm, radiation therapy, emetic agents (such as drugs and food intoxication), post-surgical studies, movement disease, among others.

Currently, diphenidol pharmaceutical forms commercially available in the market are immediate release solutions and tablets.

The drug release system plays a fundamental role in the control of the pharmacological effect, since it influences the pharmacokinetic profile, the drug release speed, on the site and duration of the pharmacological action, as well as on the side effects profile. An optimum drug release system assures this is available at the action site, with a suitable duration of the pharmacological action. Thus, the drug concentration being released in the suitable site has to be over a minimum effective concentration (MEC) and under a minimum toxic concentration (MTC) (Perri, Y. and Rades, T., Pharmaceutics drug delivery and targeting. Pharmaceutical Press, 2010).

While the action site of the majority of the drugs is not the plasma, drug concentrations are basically determined in said plasma since there is a direct relationship between drug plasma concentrations and the action site drug concentrations, which in turn is correlated to pharmacological effect and pharmacological action. Reaching the desired drug concentration in plasma and the action site depends, among other factors, on dosage frequency, drug clearance rate, administration route, and drug release system used (Perri and Rades, 2010).

The oral administration route is the most used, and the release forms of the drug administered by this route are immediate release and modified release, classified in turn as sustained release and delayed release. In the immediate release, the drug is immediately released after its administration; as the drug action time is limited to the time when the drug concentration is above the MEC, if the drug has a short half life then the re-administration range will be short and, consequently, it will require a frequent drug administration, which has a potential risk to cause low adhesion to the treatment from the patient and, therefore, an inadequate therapeutic effect. On the other hand, sustained release systems allows the releasing of the drug for extended periods of time, being able to reduce dosage frequency (Jones, D., Pharmaceuticals dosage form and design. Pharmaceutical press, 2008; Aulton, M. E., Aulton's Pharmaceutics. The design and manufacture of medicines. Churchill Linvingston Press, 2007). However, not all drugs are suitable candidates for sustained release medicaments, since drug characteristics such as dose, efficacy, solubility, stability, absorption, and presystemic and systemic metabolism have to be considered (Perri and Rades, 2010).

Diphenidol hydrochloride is well absorbed after oral administration, reaching a maximum time in plasma concentrations between 1.5 and 3 hours, while the half life is 4 hours (Hernández at al, Development of an HPLC method for determination of diphenidol in plasma and its application in an oral multi-dose bioequivalence study in a healthy female Mexican population. J. Pharm. Biomed. Anal., 2005, 38:746-750). This is the reason why the use of immediate release solutions and tablets represents certain disadvantages for the patient, for example, having to perform four intakes daily, one every 6 hours, in order to maintain the plasma concentration at systemic level in 24 hours; this intake frequency, which is established under medical prescription, may cause an overdosing or intake missing.

In order to overcome these drawbacks, modified release pharmaceutical forms have been developed.

For example, U.S. Pat. No. 5,368,861 describes a unitary preparation, which may comprise diphenidol hydrochloride as an active principle. This unitary preparation comprises a fast release portion, being used to assure the therapeutic level of a drug in a short period of time after its administration, and a sustained release portion. The preparation of this patent has, since it is in an aqueous medium, a fast disintegration of the fast release portion and it can maintain a therapeutic level of the drug in question in a short period of time after the administration.

On the other hand, U.S. Pat. No. 7,976,871 describes a dosage form comprising: a) particles in a micromatrix containing a highly soluble active ingredient and one or more hydrophobic agents to control the release; and b) a coating of the particles in the micromatrix with one or more hydrophobic agents to control the release. The dosage form may also include, optionally, one or more excipients commonly used in oral pharmaceutical formations. Diphenidol is included among the high solubility active ingredients capable of being employed in an amount lower than or equal to 1500 mg, and it may be present as a free base form or as a pharmaceutically acceptable salt. The dosage form can be made in a tablet form, and it is administered to the patient once or twice a day only. However, the process for obtaining a modified release system through a micromatrix has the drawback that numerous steps are required, such as the matrix formation, and in some cases the coating of the resulting particles, which rises the process costs.

According to the above, it may be appreciated that the modified release pharmaceutical forms known in the state of the art can be used for a great amount of active principles. However, none of them allows obtaining a pharmaceutical composition specifically designed for diphenidol, which takes its particular characteristics into account, and which results truly useful and effective.

OBJECTS OF THE INVENTION

Considering the shortcomings of the prior art, it is an object of the present invention to provide a sustained release diphenidol composition, which allows the patient to reduce the number of intakes.

It is an additional object of the present invention to provide a sustained release diphenidol composition that allows maintaining the minimum effective concentration of the active principle at plasma level.

It is another object of the present invention to provide a sustained release diphenidol composition which makes posology and drug intake management easier.

BRIEF DESCRIPTION OF THE INVENTION

For this purpose, a sustained release diphenidol pharmaceutical composition has been invented, comprising: a) from 15 to 50% diphenidol hydrochloride; b) from 0.1 to 20% of one or more binding agents; c) from 5 to 90% of one or more diluent agents; d) from 5 to 50% of one or more releasing modification agents; and) from 0.25 to 10% of one or more lubricating agents; and f) 0.1 to 10% of one or more gliding agents.

In a preferred embodiment of the invention, the sustained release diphenidol pharmaceutical composition comprises: a) from 16 to 40% diphenidol hydrochloride; b) from 0.5 to 5% povidone; c) from 0.1 to 3% sodium alginate; d) from 20 to 90% microcrystalline cellulose; e) from 20 to 90% silicified microcrystalline cellulose; f) from 5 to 50% hypromellose; from 0.25 to 5% magnesium stearate; and g) from 0.1 to 1% of silicon dioxide.

BRIEF DESCRIPTION OF THE DRAWINGS

The novel aspects considered characteristic of the present invention will be established particularity in the appended claims. However, some embodiments, characteristics and some objects and advantages thereof will be better understood from the detailed description, when read related to the appended drawings, wherein:

DETAILED DESCRIPTION OF THE INVENTION

Figure 1:
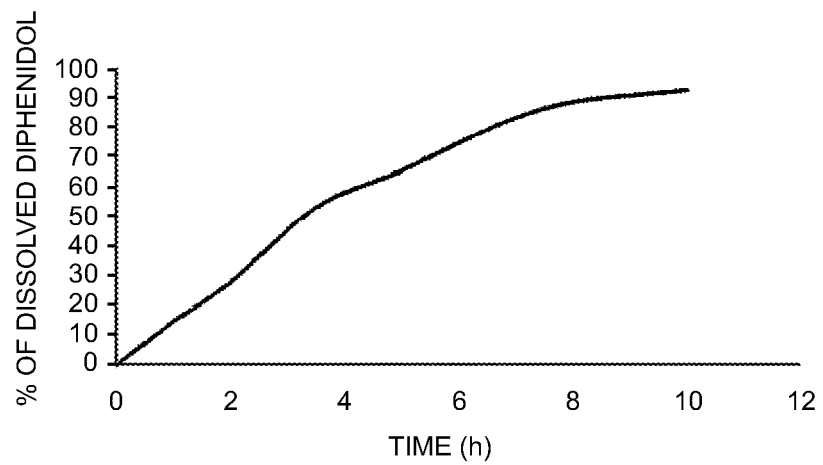
FIG. 1 is a graphic showing the tablets dissolution profile for 100 mg diphenidol according to the present invention.

It has been found that the sustained release diphenol pharmaceutical composition of the present invention allows an efficient prophylactic management for the patient, as it permits to reduce the number of daily intakes to two, maintaining the plasma drug concentration within the concentrations considered as therapeutic.

Therefore, in an aspect of the invention, a sustained release diphenidol pharmaceutical composition is described, comprising: a) from 15 to 50% diphenidol hydrochloride; b) from 0.1 to 20% of one or more binding agents; c) from 5 to 90% of one or more diluent agents; d) from 5 to 50% of one or more releasing modification agents; and) from 0.25 to 10% of one or more lubricating agents; and f) 0.1 to 10% of one or more gliding agents.

In a preferred embodiment of the invention, the binding agent is selected from the group comprising acacia gum, alginic acid, carbomer, sodium carboxymethylcellulose, copovidone, dextrine, dextrose, ethylcellulose, jelly, guar gum, hydroxyethylcellulose, hydroxyethylmethylcellulose, hydroxypropylcellulose, hypromelose, methylcellulose, povidone, sodium alginate, starch, and pregelatinized starch, preferably povidone and sodium alginate.

Likewise, the diluent agent is selected from the group comprising microcrystalline cellulose, silicified microcrystalline cellulose, a mixture of corn starch/pregelatinized starch, dextrine, dextrose, hydroxypropylcellulose, isomalt, kaolin, anhydrous lactose, lactose monohydrate, a mixture of lactose monohydrate/corn starch, a mixture of lactose monohydrate/microcrystalline cellulose, mixture of lactose monohydrate/povidone, a mixture of lactose monohydrate/cellulose dust, spray-dried lactose, magnesium carbonate, maltose, mannitol, sorbitol, starch, and pregelatinized starch, preferably microcrystalline cellulose and silicified microcrystalline cellulose.

With respect to the releasing modifying agent, this is selected from the group comprising alginic acid, carbomer, carrageenan, ethylcellulose, glyceryl monostearate, glyceryl palmitostearate, hypromellose, methylcellulose, and xanthan gum, preferably hypromellose.

The lubricating agent is selected from the group comprising calcium stearate, magnesium stearate, glyceryl monostearate, glyceryl palmitostearate, mineral oil, sodium benzoate, sodium stearyl fumarate, starch, stearic acid, talc, hydrogenated plant oil, and zinc stearate, preferably magnesium stearate.

Finally, the gliding agent is selected from silicon dioxide, colloidal silicon dioxide and talc, preferably silicon dioxide.

In a specific embodiment of the present invention, the sustained release diphenidol pharmaceutical composition comprises: a) from 16 to 40% diphenidol hydrochloride; b) from 0.5 to 5% povidone; c) from 0.1 to 3% sodium alginate; d) from 20 to 90% microcrystalline cellulose; and) from 20 to 90% silicified microcrystalline cellulose; f) from 5 to 50% hypromellose; from 0.25 to 5% magnesium stearate; and g) from 0.1 to 1% of silicon dioxide.

In a particularly preferred embodiment of the invention, said sustained release diphenidol pharmaceutical composition comprises: a) from 30 to 40% diphenidol hydrochloride; b) from 1 to 2% povidone; c) from 0.1 to 1% sodium alginate; d) from 20 to 30% microcrystalline cellulose; e) from 20 to 30% silicified microcrystalline cellulose; f) from 10 to 40% hypromellose; g) from 1 to 2% magnesium stearate; and h) from 0.1 to 0.5% silicon dioxide.

The sustained release diphenidol composition of the present invention is administered orally, and it is presented as a tablet pharmaceutical form.

After the initial administration of the sustained release diphenidol composition of the present invention, an average diphenidol plasma concentration from 40 to 46 ng/mL is reached after 1 hour; from 53 to 66 ng/mL after 2 hours; from 64 to 83 ng/mL after 3 hours; from 72 to 94 ng/mL after 4 hours; from 87 to 114 ng/mL after 6 hours; from 75 to 93 ng/mL after 8 hours; and, from 61 to 74 ng/mL after 12 hours. The composition in tablet form is obtained using techniques well known in the state of the art, including the mixing and sieving, wet granulating, drying, dry granulating, final mixing, lubrication and tabletting steps.

Likewise, with the sustained release diphenidol composition of the present invention a reduction the number of drug daily intakes is achieved compared to the existing immediate release forms, changing from 6 intakes a day, every 4 hours, to 2 intakes with longer hour space therebetween (12 hours), thus facilitating posology and intake managing of the drug. Through this, intake missing and/or overdosing is avoided. Likewise, it allows maintaining the active concentration at plasma level.

The present invention will be better understood from the following examples, which are shown for illustrative purposes only to allow proper understanding of the preferred embodiments of the present invention, without implying that there are no other embodiments non-illustrated which may be practiced based on the above disclosed detailed description.

EXAMPLES

Example 1

Making of the Sustained Release Diphenidol Composition in a Tablet Form a) Mixing and Sieving 244 silicon dioxide and PH 101 microcrystalline cellulose were mixed for 10 minutes. This mixture was sieved using a mesh, and it was placed in a 125 kg ribbon mixer.

Likewise, diphenidol hydrochlorate was sieved (in an amount enough to have an equivalent to about 100 mg of base diphenidol in the tablet obtained at the end of the process) with a mesh, with the aid of an oscillating granulator, and it was placed in the above-mentioned ribbon mixer. The above components were mixed for 15 minutes.

b) Wet Granulating

In order to prepare the binding solution, purified water was added into a container. K90 polyvinylpyrrolidone was slowly incorporated with constant stirring, obtaining a lump free solution.

This binding solution was added to the starting mixture obtained in the previous step in order to achieve its wetting, for which the ribbon mixer should be in movement.

With help of a granulator and utilizing a screen, the above mixture was let to granulate for about 10 minutes, and the wet granulated was received in stainless steel trays.

c) Drying

The trays with the granules were placed in an oven to dry the product for about 3 hours, to an approximate temperature of 55° C.±5° C.

d) Dry Granulating

Using an oscillating granulator and a mesh 30, all dry granules were granulated.

e) Final Mixing and Lubrication

In the ribbon mixer silicified microcrystalline cellulose, K 15M hydroxypropylmethylcellulose and sodium alginate were added, and they were mixed for 10 minutes.

Magnesium stearate, previously sieved with a mesh, was added to the ribbon mixer and it was mixed for 5 minutes.

f) Tabletting

The tabletting process was carried out in a tabletting machine with a tablet duster and a metal detector, obtaining a tablet free of foreign particles and imperfections, and with a brittleness non-greater than 1%.

Example 1A

Using the process described in Example 1, 250 g diphenidol hydrochloride with 190 g microcrystalline cellulose and 10 g silicon dioxide were mixed for 10 minutes. Subsequently, 50 g sodium carboxymethylcellulose sodium was dissolved in 200 mL of purified water and they were granulated with the previously obtained mixture. The granules were dried at a temperature of 60° C. until having an humidity from 2% to 6%. Once the granules were dry, they were passed through a mesh No. 16. Said granules were mixed with 300 g hydroxypropylmethylcellulose and 190 g microcrystalline cellulose for 10 minutes. Subsequently, 10 g magnesium stearate were added to the previous mixture and it was mixed for 5 minutes. The obtained mixture was tableted to a weight of 400 mg.

Example 1B

According to the process described in Example 1, 333 g diphenidol hydrochloride and 327 g lactose monohydrate and 20 g talc were mixed for 10 minutes. Subsequently, 25 g acacia gum were dissolved in 150 mL purified water and it was granulated with the previously obtained mixture. The granulated was dried at a temperature of 60° C until obtaining a humidity between 2% and 6%. Once the granulated was dry, it was passed through a mesh No. 20. Said granulated was mixed with 250 g carrageenan and 25 g polyvinylpyrrolidone for 10 minutes. Subsequently, 20 g calcium stearate were added to the previous mixture and it was mixed for 5 minutes. Finally, the mixture obtained was tableted to a 300 mg weight.

Example 1C

Using the process as described in Example 1, 286 g diphenidol hydrochloride with 102 g mannitol and 20 g silicon dioxide were mixed for 10 minutes. Subsequently, 30 g guar gum were dissolved in 150 mL purified water and it was granulated with the previously obtained mixture. The granulated was dried at a temperature of 60° C until obtaining a humidity from 2% to 6%. Once the granulated was dry, it was passed through a mesh No. 20. This granulated was mixed with 400 g alginic acid, 102 g microcrystalline cellulose and 40 g polyvinylpyrrolidone for 10 minutes. Subsequently, 20 g magnesium stearate were added to the previous mixture and it was mixed for 3 minutes. Finally, the mixture obtained was tableted to a 350 mg weight.

Example 2

Sustained Release Diphenidol Tablet Analytic Assessment 10 hours dissolution tests were carried out for the tablets containing 100 mg diphenidol, using the fluid method of simulated gastric fluid at different pH (1.2, 4.5 and 7.0) and of the simulated intestinal fluid (pH 7.5).

To this end, 6 tubes (tubes 1, 2, 3, 4, 5, and 6) were filled with 50 ml of gastric fluid, pH 1.2, previously heated to 37° C; 6 tablets were placed in a sinker, and subsequently one tablet in each releasing tube 1-6.

The tubes were tightly closed and were rotated for 1 hour. At the term of this period of time, the tubes were removed from the apparatus.

Each one of the 6 solutions was decanted in a 125 mL Erlenmeyer flask (flasks 1, 2, 3, 4, 5 and 6), with the aid of a stainless steel close mesh strainer, to avoid the passage of residues, and they were allowed to cool at room temperature, between 10 and 12 minutes.

Subsequently, each tablet residue was reincorporated in the respective releasing tube, with the aid of 50 mL medium at pH 2.5 previously heated at 37° C; the tubes were tightly capped and rotated for 1 hour.

Following the above procedure, the changing of buffer solutions continued according to the extraction media schedule, also considering the periods of time shown in Table 1

TABLE 1

Samples treatment conditions in the dissolution tests

| Sampling time (hours) | Time (hours) | Volume (mL) | pH |
|---|---|---|---|
| 1.0 | 1.0 | 50 | 1.2 |
| 2.0 | 1.0 | 50 | 2.5 |
| 3.5 | 1.5 | 50 | 4.5 |
| 5.0 | 1.5 | 50 | 7.0 |
| 7.5 | 2.5 | 50 | 7.5 |
| 10.0 | 2.5 | 50 | 7.5 |

Finally, equal volumes of the standard preparation and the sample preparation were separately injected (20 μL) into the chromatographer, the chromatograms were registered, and the responses of the main peaks were measured.

The behavior of the sustained release diphenidol composition, in the tablet form, is shown in FIG. 1, wherein it can be seen that during the course of the hours the active ingredient concentration is maintained at 90% or more between hours 7.5 to 10; this means that the sustained release tablet keeps the total load of the active ingredient at the term of 10 hours from the administration.

Example 3

Bioavailability Comparison Between Immediate Release Diphenidol Tablets and Sustained Release Diphenidol Tablets A study with two groups of patients was carried out in order to compare the bioavailability of an initial dose and repeated doses of two diphenidol pharmaceutical products for oral administration: commercial immediate release tablets (product A) and modified release tablets obtained according to the present invention (product B), in order to compare their different pharmacokinetic parameters between the initial dose and the steady state, and to determine If product B can be considered as a sustained release medicament.

Each group consisted of 16 healthy volunteers, male, with an average age and weight average of 27.8 years and 70 kg, respectively. Determination of the suitable sample size was made and adjusted according to the confidence intervals in other bioequivalence studies reported in the literature (Diletti et al., 1991). The considered sample size for this study was 14 subjects plus two volunteers that were considered in the randomization as a caution measure for a possible volunteer abandonment or removal, in order to have a total of 16 male subjects.

Volunteers gave their written informed consent to participate in the study. All volunteers were found in a good health state, as was determined by the medical history, medical exam and clinical laboratory tests.

The study was monocentral, prospective, longitudinal, single blind, of repeated dose, with two treatments, two periods (two sequences), crossed, balanced, with random distribution of the two possible sequences, with a drug clearance period (washing) of 13 days.

Group A was administered a 25 mg immediate release diphenidol tablet (product A), every 6 hours over three days. The last administration of this product was after 66 hours, and 12 tablets of 25 mg each were administered over this period of time.

On the other hand, group B was administered a 100 mg sustained release diphenidol tablet (product B), according to the present invention, every 12 hours over 3 days.

Volunteers were fasted at least 10 hours before initial administration of the drugs and they had breakfast four hours after the medicament intake. One of the two formulations was administered in each period to half of the subjects and the other to the rest; the same procedure was reversely repeated thirteen days later. The tablets were orally administered with 250 ml of water.

In each period 24 blood samples from the patients were taken at the following times: Predoses (time 0) and 1.0, 1.5, 2.0, 2.5, 3.0, 4.0, 6.0, 8.0, 12.0, 16.0, 24.0, 48.0, 49.0, 49.5, 50.0, 50.5, 51.0, 52.0, 54.0, 56.0, 60.0, 64.0 and 72.0 hours after the first administration of the medicament; blood samples were maintained in a freezer during sampling, at a temperature between −20° C to −28° C, and later they were stored in a super-freezer at −70° C until their transportation to the analytical unit, where they were kept at the same temperature.

The total blood volume collected from each volunteer was of 240 mL per period of study, for a total of 480 mL of blood for both periods.

Likewise, vital signs were obtained (blood pressure, heart rate, respiratory rate, and body temperature) at the following times: prior to the administration of the medicament (at least 30 minutes before placement of the catheter in the arm veins, time 0) and during the study, immediately before or after obtaining the blood sample, at 2.0, 3.0, 6.0, 8.0, 12.0, 24.0, 48.0, 50.0, 51.0, 54.0, 56.0, 60.0 and 72.0 hours after the administration of the medicaments under study.

For the analysis of the biological samples a high performance liquid chromatography method was used (HPLC) coupled to mass spectrometry.

With the results of the plasma concentrations individual diagrams were plotted (not shown) of plasma concentration vs. time for each subject and for each formulation. From those diagrams both maximum concentration ($C_{max}$) and the time to reach said concentration ($T_{max}$) were obtained, as well as other pharmacokinetic parameters. The area under the curve of the plasma concentrations vs. time (AUC) was obtained by the trapezoid method. Likewise, the individual parameters were analyzed carrying out a one tail t-test or a variance analysis (ANOVA) in order to establish the significance among the pharmacokinetic parameters.

The statistical analysis was carried out with the 16 subjects in each group. Immediate release diphenidol administration every 6 hours (product A), or that of the sustained release diphenidol of the present application every 12 hours (product B), did not clinically modify the vital signs in any of the two groups. Blood pressure, both diastolic and systolic, was not significantly clinically modified in any of the two groups along the 72 hours of the study. Likewise, no clinically significant changes in heart rate, respiratory rate and body temperature were present by comparing both groups (A and B) which received the diphenidol formulations.

Figure 2:
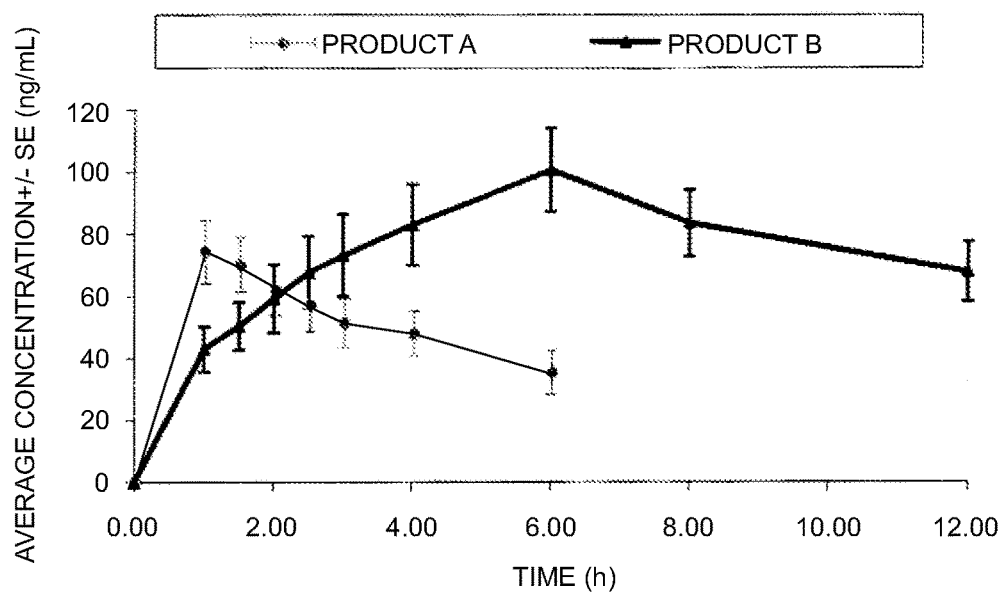
FIG. 2 shows the average pharmacokinetic profile for the initial dose of product A of immediate release diphenidol, at a dose of 25 mg, as well as of product B of sustained release diphenidol, at a dose of 100 mg, ±standard error.

On the other hand, in group B, repeated diphenidol administration caused two adverse events in one of the volunteers. After initial administration of product A within the first 6 hours and of product B within the first 12 hours, plasma concentrations of both products were increased reaching a $C_{max}$ (±standard error) of 79.54±9.37 and 108.83±13.87 ng/ml, at a time ($T_{max}$) of 1.46±0.12 and 5.96±0.58 h, for diphenidol formulations A and B, respectively (see FIG. 2); that is to say, the levels and variability (standard error) reached by the sustained release diphenidol composition of the present invention (product B), are similar to that shown by the immediate release product (product A).

The area under the curve, $AUC_{0-t}$ (±standard error) obtained for products A and B was 279.61±42.48 and 868.64±114.63 h*ng/ml, respectively. Also, the area under the curve ($AUC0_{-\infty}$) obtained for products A and B was 596.65±138.59 and 14030.24±12126.03 h*ng/ml, respectively. Likewise, the clearance half life, graphically calculated, in this case was of 4.5 hours for product A and of 18 hours for product B. The calculated clearance was of 96010.47±20525.70 mL/h and of 18587.90±4747.94 mL/h for drugs A and B respectively.

Figure 3:
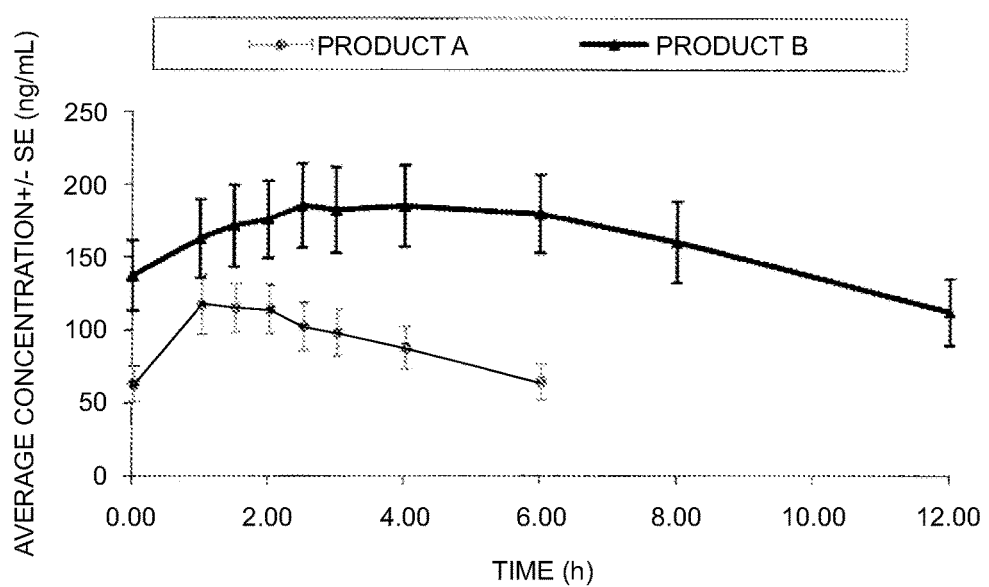
FIG. 3 shows a comparison of the plasma concentrations of diphenidol in steady state for product A of immediate release, after the administration of 9 doses (one every 6 hours), as well as for product B of sustained release after 5 doses (one every 12 hours), ±standard error. Real times of the study in the steady state correspond to 48, 50, 52, 54, 56, 58 and 60 hours, but for comparison purposes, similar times to those in the initial state were considered.

Three days after repeated administration every 6 hours of product A (or every 12 hours of product B, i.e., at the start of the steady state), plasma concentrations of both pharmaceutical preparations were increased reaching a $C_{max}$ (±standard error) of 126.84±19.69 and 202.95±29.46 ng/ml, at a time ($T_{max}$) of 1.46±0.11 and 4.46±0.45 h, for diphenidol formulations A and B, respectively (see FIG. 3), with a $C_{min}$ (±standard error) of 63.16±12.04 and 136.43±25.87 ng/ml, and with a $C_{average}$ of 92.57±15.15 and 161.15±26.36 for products A and B, respectively.

The area under the curve, $AUC_{0-t}$ (±standard error) obtained for products A and B was of 555.42±90.90 and 1933.93±316.26 h*ng/ml, respectively. Also, the fluctuation % obtained for the formulations A and B was of 76.68±7.46 and 48.45±4.79, respectively, as well as the Swing that was 1.31.77±0.18 for product A and 0.66±0.35 for product B.

The initial dose pharmacokinetic parameters versus the steady state were statistically compared in order to establish whether the studied products are different in their initial state and in their steady state, as well as to establish the difference therebetween. The pharmacokinetic parameters compared were the $C_{max}$ and the AUC (see Table 2 and Table 3), since the former is an indicative of the absorption rate while the second is an indicative of the drug amount being absorbed (Steinijans et al., 1992).

TABLE 2

Comparison between diphenidol maximum concentration during the initial dose and in the steady state, comparison of B/A differences

| Diphenidol initial dose $C_{max}$ | | | Diphenidol steady state $C_{max}$ | | |
| --- | --- | --- | --- | --- | --- |
| Product A (ng/mL) | Product B (ng/mL) | B/A | Product A (ng/mL) | Product B (ng/mL) | B/A |
| 147.9125 | 170.7356 | 1.1543 | 360.2218 | 497.9994 | 1.3825 |
| 53.9664 | 54.2568 | 1.0054 | 82.41 | 215.8197 | 2.6189 |
| 77.663 | 218.6172 | 2.8149 | 106.6397 | 220.7502 | 2.0701 |
| 32.118 | 78.3431 | 2.4392 | 49.0286 | 96.3019 | 1.9642 |
| 69.1666 | 62.2134 | 0.8995 | 100.8437 | 138.765 | 1.3760 |
| 111.8626 | 189.0888 | 1.6904 | 164.1344 | 366.6689 | 2.2340 |
| 83.0008 | 114.9722 | 1.3852 | 99.7371 | 154.2428 | 1.5465 |
| 140.9735 | 143.2165 | 1.0159 | 234.6305 | 342.3684 | 1.4592 |
| 92.7631 | 124.1497 | 1.3384 | 113.8533 | 179.8427 | 1.5796 |
| 87.5666 | 154.5041 | 1.7644 | 129.7107 | 218.8461 | 1.6872 |
| 78.7114 | 80.1024 | 1.0177 | 135.0999 | 97.6063 | 0.7225 |
| 26.4753 | 45.8966 | 1.7336 | 47.9335 | 83.2182 | 1.7361 |
| 120.5518 | 131.0562 | 1.0871 | 147.985 | 238.1693 | 1.6094 |
| 24.306 | 30.0658 | 1.2370 | 38.4005 | 66.4078 | 1.7293 |
| 52.5041 | 65.9479 | 1.2561 | 95.2669 | 226.9079 | 2.3818 |
| 73.2204 | 78.1861 | 1.0678 | 123.6936 | 103.2604 | 0.83 |
| AVERAGE 79.5476 | AVERAGE 108.8345 | AVERAGE 1.4317 | AVERAGE 126.8493 | AVERAGE 202.9484 | AVERAGE 1.6833 |

As can be seen in Table 2, the comparison between the maximum plasma concentrations at the initial dose and the steady state dose of product A is statistically different (p<0.05).

Likewise, maximum plasma concentrations of the sustained release product of the present invention, product B, are statistically different between the initial dose and the final dose in the steady state. The comparison between the maximum plasma concentrations ($C_{max}$) of product A and B is obviously different at the initial and steady state doses, basically due to the difference in the administered dose. The same occurs with AUC (Table 3).

TABLE 3

Comparison between the area under the curve from 0 to T during diphenidol initial and steady state dose, comparison of the B/A differences

| Diphenidol initial dose $ABC_{0\ to\ t}$ | | | Diphenidol at steady state $ABC_{0\ to\ t}$ | | |
|---|---|---|---|---|---|
| Product A (h * ng/ml) | Product B (h * ng/ml) | B/A | Product A (h * ng/ml) | Product B (h * ng/ml) | B/A |
| 447.8722 | 1553.0780 | 3.4677 | 1516.2779 | 5429.3156 | 3.5807 |
| 147.2396 | 423.9856 | 2.8796 | 336.1972 | 1921.8737 | 5.7165 |
| 230.7908 | 1231.9354 | 5.3379 | 471.8479 | 2159.5609 | 4.5768 |
| 121.7487 | 555.6273 | 4.5637 | 204.9404 | 896.5754 | 4.3748 |
| 172.2713 | 481.8144 | 2.7968 | 436.5301 | 1275.3413 | 2.9215 |
| 497.3179 | 1588.0061 | 3.1931 | 861.8611 | 3298.4884 | 3.8272 |
| 399.2139 | 1128.8113 | 2.8276 | 497.5336 | 1459.9769 | 2.9344 |
| 640.6318 | 1355.7812 | 2.1163 | 1199.6340 | 3547.3772 | 2.9570 |
| 431.2187 | 1175.7998 | 2.7267 | 588.9491 | 1898.4416 | 3.2234 |
| 377.7014 | 1312.1187 | 3.4740 | 570.5364 | 1985.8021 | 3.4806 |
| 264.3500 | 502.6939 | 1.9016 | 527.4121 | 815.7433 | 1.5467 |
| 54.9248 | 297.0717 | 5.4087 | 182.0990 | 713.9833 | 3.9209 |
| 272.9094 | 826.4490 | 3.0283 | 553.4196 | 2017.4649 | 3.6455 |
| 44.5532 | 236.0890 | 5.2990 | 157.8977 | 626.4970 | 3.9677 |
| 175.6578 | 574.6456 | 3.2714 | 359.5580 | 1997.6456 | 5.5558 |
| 195.3807 | 654.4197 | 3.3495 | 422.1074 | 897.3500 | 2.1259 |
| AVERAGE 279.6114 | AVERAGE 868.6454 | AVERAGE 3.4776 | AVERAGE 555.4251 | AVERAGE 1933.8398 | AVERAGE 3.6472 |

Similarly, as can be seen in Table 3, the AUC from $_{0\ to\ t}$ is statistically different between the initial dose and the steady state dose for products A or B. The difference between B/A in $C_{max}$ and the AUC from $_{0\ to\ t}$ is similar when comparing the initial dose and the steady state dose, although it is greater with the AUC from $_{0\ to\ t}$. On the other hand, averages of the minimum plasma concentrations are similar after 24 hours and 48 hours from the treatment, for both product A and product B.

According to the above results, no differences were seen in the demographic aspects in the average of the subjects participating in the study (groups A and B), in fact, those receiving product A were similar in weight, size, BMI and age to those who received product B in any period. The above suggests a proper randomization of the subjects.

On the other hand, vital signs were not modified in a significant clinically manner. A slight body temperature increase was seen in volunteers from both group A and group B, which may be due to a mild pharmacological effect with non-clinical importance which is similar for both drugs and which has not been disclosed in the literature, or on the contrary, as there were no volunteers receiving placebo, the occurring of a circadian rhythm in the body temperature may not be discarded, as has been repeatedly indicated in the literature (Waterhouse et al, The circadian rhythm of core temperature: Origin and some implications for exercise performance. Chronobiol. Int., 2005, 22:207-225) and which is not modified by diphenidol. However, the effect in the body temperature is minimal, and it does not have clinical significance.

Likewise, administration of diphenol at doses of 25 mg in immediate release tablets (product A), every 6 hours, and at doses of 100 mg in sustained release tablets (product B), every 12 hours, did not produce clinically significant changes in vital signs when they were evaluated as an average. It is worth mentioning that two adverse events were suffered by a subject in group B, probably not related to the administration of a single diphenidol dose in 100 mg sustained release tablets every 12 hours, which coincides with previous reports on adverse effects in healthy volunteers under the administration of single doses of medicaments for bioequivalence studies. (Lujan et al, Adverse events associated with the single use of drugs. International Society of Pharmacovigilance Annual Conference. Pharmacovigilance into the future. Amsterdam, Oct. 16-19 2002).

Likewise, a statistically significant difference between the $C_{max}$ achieved among both products could be observed in this study, product B having a higher $C_{max}$ which is statistically different from product A (p<0.05). This difference is due basically to the administered dose. Likewise, the $T_{max}$ is lower for the reference product (product A) (p<0.05).

Thus, it can be concluded that products A and B for oral administration in tablets are not bioequivalent and they show obvious differences in their $C_{max}$, $T_{max}$, AUC y $V_{1/2}$, which is to be expected due to the difference in the administered dose. However, it was clearly seen that both products A and B reach a steady state in 3 days. Likewise, the results show that product B has the sustained release product features, and it is different from an immediate release product (product A). Likewise, both medicaments, the immediate release at a 25 mg dose every 6 hours (product A) and the sustained release at a 100 mg dose every 12 hours (product B) reach concentrations reported within therapeutic ones, ranging from 120 mg every 24 hours to 300 mg every 24 hours (Hernández et al., 2005, USP DL, 2000), in both the initial dose and the steady state. Product B clearly showed being a sustained release medicament which may be used as an every-12-hours administration.

According to the above-described, it may be seen that the sustained release diphenidol composition has been envisioned to facilitate posology and management of the drug intake, maintaining the active ingredient concentration at plasma level, and it will be apparent to any person skilled in the art that the embodiments of the sustained release diphenidol composition according the above description, are illustrative only and non-limiting of the present invention, since numerous consideration changes in its details are possible without departing from the scope of the invention.

Therefore, the present invention should not be considered restricted except by the prior art demands and by the scope of the appended claims.

The invention claimed is:

1. A sustained release diphenidol single layer tablet, consisting of: a) from 15 to 50% diphenidol hydrochloride;

b) from 0.1 to 20% of one or more binding agents; c) from 5 to 90% of one or more diluent agents; d) from 5 to 50% of one or more release modification agents; e) from 0.25 to 10% of one or more lubricating agents; and f) 0.1 to 10% of one or more gliding agents, wherein all of the ingredients of the tablet are mixed together prior to tabletting.

2. The single layer tablet according to claim 1, wherein the binding agent is selected from the group comprising acacia gum, alginic acid, carbomer, sodium carboxymethylcellulose, copovidone, dextrine, dextrose, ethylcellulose, jelly, guar gum, hydroxyethylcellulose, hydroxyethylmethylcellulose, hydroxypropylcellulose, hypromelose, methylcellulose, povidone, sodium alginate, starch, and pregelatinized starch.

3. The single layer tablet according to claim 2, wherein the binding agent is selected from povidone and sodium alginate.

4. The single layer tablet according to claim 1, wherein the diulent agent is selected from the group comprising microcrystalline cellulose, silicified microcrystalline cellulose, a mixture of corn starch/pregelatinized starch, dextrine, dextrose, hydroxypropylcellulose, isomalt, kaolin, anhydrous lactose, lactose monohydrate, a mixture of lactose monohydrate/corn starch, a mixture of lactose monohydrate/microcrystalline cellulose, mixture of lactose monohydrate/povidone, a mixture of lactose monohydrate/cellulose dust, spray-dried lactose, magnesium carbonate, maltose, mannitol, sorbitol, starch, and pregelatinized starch.

5. The single layer tablet according to claim 4, wherein the diluent agent is selected from microcrystalline cellulose and silicified microcrystalline cellulose.

6. The single layer tablet according to claim 1, wherein the releasing modification agent is selected from the group comprising alginic acid, carbomer, carrageenan, ethylcellulose, glyceryl monostearate, glyceryl palmitostearate, hypromellose, methylcellulose, and xanthan gum.

7. The single layer tablet according to claim 6, wherein the releasing modification agent is hypromellose.

8. The single layer tablet according to claim 1, wherein the lubricating agent is selected from the group comprising calcium stearate, magnesium stearate, glyceryl monostearate, glyceryl palmitostearate, mineral oil, sodium benzoate, sodium stearyl fumarate, starch, stearic acid, talc, hydrogenated plant oil, and zinc stearate.

9. The single layer tablet according to claim 8, wherein the lubricating agent is magnesium stearate.

10. The single layer tablet according to claim 1, wherein the gliding agent is selected from silicon dioxide and talc.

11. The single layer tablet according to claim 10, wherein the gliding agent is silicon dioxide.

12. The single layer tablet according to claim 1, consisting of: a) from 16 to 40% diphenidol hydrochloride; b) from 0.5 to 5% povidone; c) from 0.1 to 3% sodium alginate; d) from 20 to 90% microcrystalline cellulose; e) from 20 to 90% silicified microcrystalline cellulose; f) from 5 to 50% hypromellose; from 0.25 to 5% magnesium stearate; and g) from 0.1 to 1% of silicon dioxide.

13. The single layer tablet according to claim 12, consisting of: a) from 30 to 40% diphenidol hydrochloride; b) from 1 to 2% povidone; c) from 0.1 to 1% sodium alginate; d) from 20 to 30% microcrystalline cellulose; e) from 20 to 30% silicified microcrystalline cellulose; f) from 10 to 40% hypromellose; g) from 1 to 2% magnesium stearate; and h) from 0.1 to 0.5% of silicon dioxide.

14. The single layer tablet, claim 1, which is orally administered.

15. The single layer tablet claim 1, wherein once initial administration of the composition is carried out, the diphenidol plasma concentration profile being reached is from 40 to 46 ng/mL after 1 hour; from 53 to 66ng/mL after 2 hours; from 64 to 83 ng/mL after 3 hours; from 72 to 94 ng/mL after 4 hours; from 87 to 114 ng/mL after 6 hours; from 75 to 93 ng/mL after 8 hours; and, from 61 to 74ng/mL after 12 hours.

* * * * *